US007838685B2

(12) United States Patent
Takeoka et al.

(10) Patent No.: US 7,838,685 B2
(45) Date of Patent: Nov. 23, 2010

(54) CATIONIC AMINO ACID TYPE LIPID (75) Inventors: Shinji Takeoka, 3-40-16-404, Tamagawa, Setagaya-ku, Tokyo 158-0094 (JP); Yosuke Obata, Tokyo (JP)

(73) Assignee: Shinji Takeoka, Tokyo (JP)

( * ) Notice: Subject to any disclaimer, the term of this patent is extended or adjusted under 35 U.S.C. 154(b) by 0 days.

(21) Appl. No.: 11/919,286

(22) PCT Filed: Apr. 27, 2006

(86) PCT No.: PCT/JP2006/309211

§ 371 (c)(1),
(2), (4) Date: May 8, 2008

(87) PCT Pub. No.: WO2006/118327

PCT Pub. Date: Nov. 9, 2006

(65) Prior Publication Data

US 2009/0012306 A1  Jan. 8, 2009

(30) Foreign Application Priority Data

Apr. 27, 2005 (JP) ............... 2005-130024

(51) Int. Cl.
*C07D 233/61* (2006.01)
(52) U.S. Cl. .................... 548/335.5; 554/106
(58) Field of Classification Search ............. 548/335.5; 554/106
See application file for complete search history.

(56) References Cited

U.S. PATENT DOCUMENTS 4,866,035 A  9/1989  Durette

2006/0008472 A1  1/2006  Huang et al.

FOREIGN PATENT DOCUMENTS

| EP | 1 340 740 A1 | 9/2003 |
| GB | 1 570 625 A | 12/1976 |
| JP | 52-73820 | 6/1977 |
| JP | 59-139384 A | 8/1984 |
| JP | 2-69449 A | 3/1990 |

(Continued)

OTHER PUBLICATIONS

Kim et al. (Bioconjugate Chem., vol. 15, No. 5, 2004, pp. 1095-1101).*

(Continued)

*Primary Examiner*—Kamal A Saeed
*Assistant Examiner*—Valerie Rodriguez-Garcia
(74) *Attorney, Agent, or Firm*—Birch, Steward, Kolasch & Birch, LLP.

(57) ABSTRACT

The present invention provides a novel complex lipid having a cationic functional group derived from an amino acid. Namely, the present invention provides a cationic acid amino acid type lipid represented by the following formula:

$$R^1-\overset{O}{\underset{\|}{C}}-\overset{H}{\underset{|}{N}}-HC\overset{A^1-R^2}{\underset{(CH_2)_n-A^2-R^3}{\diagdown}} \quad (I)$$

wherein, $R^1$ is a hydrocarbon group having a cationic functional group derived from an amino acid, $R^2$ and $R^3$ are each independently a chain hydrocarbon group, $A^1$ and $A^2$ are each independently a linkage group selected from the group consisting of —COO—, —OCO—, —CONH— and NHCO—, and n is an integer of 2 to 4.

6 Claims, 6 Drawing Sheets

FOREIGN PATENT DOCUMENTS

| | | | |
|---|---|---|---|
| JP | 2001-64383 A | | 3/2001 |
| JP | 2003-64037 | * | 3/2003 |
| JP | 2003-64037 A | | 3/2003 |
| WO | WO 94/24154 | * | 4/1994 |
| WO | WO 94/24154 | * | 10/1994 |
| WO | WO-02/38530 A1 | | 5/2002 |

OTHER PUBLICATIONS

Du Vigneaud et al. (J. Am. Chem. Soc. 1957, 79, 5572-5575).*

Kim et al., *Bioconjugate Chem.*, vol. 15, No. 5, 2004, pp. 1095-1101.

Ihara, Hirotaka et al., "Novel self-assembling organogelators by combination of a double chain-alkylated l-glutamide and a polymerichead group". (2003), 1 (17), 3004-3006.

Seong, Hasoo et al., "Preparation of liposomes containing dibranched-amino acids and characterization of their glucose-binding properties". (2000), 41 (2), 1655-1656.

Ihara, Hirotaka et al., "Production of helical bilayer membranes from L-glutamic acid derivatives with bis (dodecylamide) groups and their specific optical activity". (1990), (10), 1047-53.

Hachisako, Hiroshi et al., "Chirally arranged monomeric dyes on helical bilayer membranes, Liquid Crystals". (1993), 13 (2), 307-11.

Yamada, Norihiro et al., "Regulation of β-Sheet Structures within Amyloid-Like β-Sheet Assemblage from Tripeptide Derivatives". (1998), 120 (47), 12192-12199.

Lefrancier, P. et al., "Synthesis of N-acetyl-muramyl-L-alanyl-D-isoglutamine, an adjuvant of the immune response, and of some N-acetyl-muramyl-peptide analogs". (1977), 9 (4), 249-57.

Neumann, Klaus W. et al., "A stereocontrolled synthetic approach to glycopeptides corresponding to the carbo hydrate-protein linkage region of cell-surface proteoglycans". (1995), 3 (12), 1637-50.

Hanabusa, Kenji et al., "Low molecular weight gelators for organic fluids". (2000), 224 (2), 231-244.

* cited by examiner

CATIONIC AMINO ACID TYPE LIPID

TECHNICAL FIELD

The present invention relates to a complex lipid having a cationic functional group derived from an amino acid.

BACKGROUND ART

Technologies for encapsulating a useful substance in a liposome, which is a vesicle formed of an artificial bilayer, are actively studied in the fields of pharmaceutical drugs, cosmetics, foods, dyes and the like.

Widely used lipids for forming a layer of a liposome include, for example, a combined lipid of a layer-forming lipid such as diacylphosphatidylcholine, cholesterol or the like and a negatively charged phospholipid such as diacylphosphatidylglycerol, diacylphosphatidylinositol, diacylphosphatidylserine or the like.

It is relatively easy to produce a liposome formulation which can suppress the in vivo decomposition or control the in vivo kinetics of a drug when administered to a living organism, but it is quite difficult to construct a formulation having properties which can also improve the intracellular migration capability of a drug. The reason for this is that a liposome formulation is intended to improve the drug concentration in the vicinity of a target tissue or cell by controlling the in vivo kinetics of the drug encapsulated therein, and the ease of migration into the cell depends on the permeability of a particular drug through the bilayer of the liposome and the cell membrane. When the target is a phagocyte such as a macrophage, a monocyte or the like, however, the intracellular migration capability of the drug may occasionally be improved because the phagocyte easily takes in a microparticle such as a liposome or the like.

Recently, it has been studied to introduce a gene into a cell by forming a complex of the gene and an independent cationic lipid or a liposome containing the cationic lipid. However, use of such a carrier having an intracellular migration capability has problems that (1) it is difficult to synthesize a cationic lipid, (2) the resultant formulation is expensive, and (3) the carrier has a high level of cytotoxicity.

As a cationic lipid, an amino acid type lipid containing dialkylaspartic acid linked to lysine has been reported (Hong Sung Kim et al., Gene-Transferring Efficiencies of Novel Diamino Cationic Lipids with Varied Hydrocarbon Chans, *Bioconjugate Chem.* 2004, 15, 1095). However, this lipid has problems of being unlikely to assume a vesicle structure easily and being unstable in a dispersed state.

In view of the above-described situations, it is desired to develop a cationic lipid which (1) is easy to be synthesized, (2) can be provided at low cost, and (3) is highly biocompatible, i.e., is low in toxicity.

DISCLOSURE OF THE INVENTION

As a result of active studies in view of the above-described situations, the present inventors successfully synthesized a complex lipid having a cationic functional group derived from an amino acid.

The present invention provides a cationic amino acid type lipid as described below.

(1) A cationic amino acid type lipid represented by general formula (I):

wherein, $R^1$ is a hydrocarbon group having a cationic functional group derived from an amino acid, $R^2$ and $R^3$ are each independently a chain hydrocarbon group, $A^1$ and $A^2$ are each independently a linkage group selected from the group consisting of —COO—, —OCO—, —CONH— and NHCO—, and n is an integer of 2 to 4.

(2) The cationic amino acid type lipid according to item (1), wherein the cationic functional group is selected from the group consisting of amino group, guanidino group, imidazole group and a derivative thereof.

(3) The cationic amino acid type lipid according to item (1) or (2), wherein $R^1$ is represented by either one of formulas (a), (b) and (c):

(4) The cationic amino acid type lipid according to any one of item (1) to (3), wherein $A^1$ and $A^2$ are both —COO—.

(5) The cationic amino acid type lipid according to any one of item (1) to (4), wherein $R^2$ and $R^3$ are each independently a chain hydrocarbon group including a main chain having a carbon number of 12 to 30, the chain hydrocarbon group optionally having a substituent selected from the group consisting of alkyl group, alkenyl group, alkynyl group, isoprenoid group, carboxyl group, hydroxyl group, amino group and mercapto group.

(6) The cationic amino acid type lipid according to any one of item (1) to (5), wherein $R^2$ and $R^3$ are each independently an all chain having a carbon number of 12 to 22.

(7) The cationic amino acid type lipid according to any one of item (1) to (6), wherein n is 2.

(8) A cationic amino acid type lipid represented by either one of formulas (I)-1, (I)-2 and (I)-3:

(I)-1

(I)-2

(I)-3

(9) A molecular assembly including the cationic amino acid type lipid according to any one of item (1) to (8).

A cationic amino acid type lipid according to the present invention is produced with easily available materials and is easy to be synthesized, and thus it can be synthesized in a large quantity at low cost. According to a preferable embodiment of the present invention, a cationic lipid according to the present invention, when used as a component of a micelle, a lipid microsphere, a liposome or other formulations, can contribute to the production of a formulation having a very high intracellular migration capability by improving the affinity of the formulation to the cell. A cationic amino acid type lipid according to the present invention also has a high capability of being formed into a vesicle and thus it can stably encapsulate a useful substance therein. A cationic amino acid type lipid according to the present invention is highly biodegradable, and is also low in toxicity because substances obtained by the biodegradation are an amino acid or a derivative thereof, long-chain alcohol and the like. Accordingly, a cationic amino acid type lipid according to the present invention is useful as a component of a stable, safe and functional carrier of a substance having an efficacy in pharmaceutical drugs, reagents, cosmetics and the like.

BEST MODE FOR CARRYING OUT THE INVENTION

Hereinafter, a cationic amino acid type lipid according to the present invention and a molecular assembly including the same will be described in detail.

A. Cationic Amino Acid Type Lipid

A cationic amino acid type lipid according to the present invention is represented by the following general formula (I):

(I)

wherein, $R^1$ is a hydrocarbon group having a cationic functional group derived from an amino acid, $R^2$ and $R^3$ are each independently a chain hydrocarbon group, $A^1$ and $A^2$ are each independently a linkage group selected from the group consisting of —COO—, —OCO—, —CONH— and NHCO—, and n is an integer of 2 to 4.

In formula (I), $R^1$ is a hydrocarbon group having a cationic functional group derived from an amino acid. Herein, the term "cationic functional group" refers to any group exhibiting a cationic property in an aqueous solution, with no specific limitation. Examples of the cationic functional group include amino group, guanidino group, imidazole group, and derivatives thereof. Examples of the "derivatives" include compounds obtained as a result of a hydrogen atom contained in an amino group, a guanidino group or an imidazole group being substituted with a substituent such as lower alkyl group (methyl, ethyl, propyl, isopropyl, n-butyl, sec-butyl, etc.), aminoalkyl group (aminomethyl, aminoethyl, aminopropyl, aminobutyl, etc.) and corresponding oligoaminoalkyl group, hydroxyl group, hydroxyalkyl group (hydroxymethyl, hydroxyethyl, hydroxypropyl, etc.), oligooxyalkyl group (oligooxymethyl group, oligooxyethyl group, oligooxypropyl, etc.) or the like.

$R^1$ may have at least one cationic functional group, but preferably has two or more cationic functional groups. A compound having two or more cationic functional groups can stably form a complex with a nucleic acid such as a DNA or an RNA, which is a polyanion. A compound having two or more cationic functional groups is also preferable in being stably linked to an area of a cell surface where negative charges are concentrated, which improves the intracellular migration capability. Where the compound has two or more cationic functional groups, there is no specific limitation on the combination thereof.

Among the above-listed groups, $R^1$ is preferably a group represented by any one of the formulas (a), (b) and (c).

In formula (I), $R^2$ and $R^3$ are each independently a chain hydrocarbon group. There is no specific limitation oh the "chain hydrocarbon group" as long as the chain hydrocarbon group is a hydrophobic group which can be introduced by covalent bond to the linkage group $A^1$ or $A^2$. The chain hydrocarbon group may be either of straight chain or branched chain, but is preferably of straight chain. The number of carbon atoms in the main chain of the chain hydrocarbon group is preferably 12 to 30, and is more preferably 12 to 22. In the case where the chain hydrocarbon group has an unsaturated bond(s) such as a double bond or a triple bond, the number of the unsaturated bond(s) is preferably 1 to 4. The main chain of the chain hydrocarbon group is preferably an alkyl chain, an alkenyl chain or an alkynyl chain, and is more preferably alkyl chain.

The chain hydrocarbon group may have a substituent selected from the group consisting of alkyl group, alkenyl group, alkynyl group, isoprenoid group, carboxyl group, hydroxyl group, amino group, and mercapto group. The alkyl group preferably has a carbon number of 1 to 6, and examples of such an alkyl group include methyl group, ethyl group, propyl group, isopropyl group, n-butyl group, sec-butyl group, tert-butyl group, pentyl group, hexyl group and the like. The alkenyl group preferably has a carbon number of 1 to 6, and examples of such an alkenyl group include vinyl group, allyl group, propenyl group, isopropenyl group, 2-butenyl group and the like. The alkynyl group preferably has a carbon number of 1 to 6, and examples of such an alkynyl group include ethynyl group, propynyl group, butynyl group and the like.

Among the above-listed groups, $R^2$ and $R^3$ are each preferably an alkyl group having a carbon number of 12 to 22 which may optionally have a substituent.

In formula (I), $A^1$ and $A^2$ are each independently a linkage group selected from the group consisting of —COO—, —OCO—, —CONH— and NHCO—. $A^1$ and $A^2$ may be any of these linkage groups with any combination with no specific limitations but it is preferable that $A^1$ and $A^2$ are both —COO—.

In formula (I), n is an integer of 2 to 4. It is preferable that n is an integer of 2 to 4 because in such a case, the chain hydrocarbon group of the compound represented by formula (I) can be aligned in the bilayer generally vertical to the surface. In addition, where n is an integer of 2 to 4, the hydrophilic-hydrophobic interface of the bilayer formed of an assembly of cationic amino acid type lipids in an aqueous solution is stable and thus a vesicle structure is likely to be formed. Therefore, the compound represented by formula (I), when used as a lipid component of the molecular assembly, is expected to have an effect of stabilizing the vesicle structure and also the dispersed state. It is more preferable that n is 2 because this allows glutamic acid or a derivative thereof to be usable as a material of the compound represented by formula (I), which realizes low cost and low toxicity, in addition to providing the above-described effects.

Specifically, a cationic amino acid type lipid according to the present invention is preferably a compound represented by the following formula (I)-1, (I)-2 or (I)-3.

(Production Method)

Such a cationic amino acid type lipid can be produced very easily by combining known reactions. For example, a cationic amino acid type lipid according to the present invention can be produced by sequentially reacting a trifunctional core compound having the following formula with a source of a chain hydrocarbon group and with a source of a hydrocarbon group having a cationic functional group:

wherein, $A^{11}$ and $A^{12}$ are each independently a carboxyl group, a hydroxyl group, or an amino group, and n is an integer of 2 to 4.

A representative synthetic route for producing a cationic amino acid lipid according to the present invention is as follows.

First, the $A^{11}$ or $A^{12}$ part of the trifunctional core compound is reacted with a source of a chain hydrocarbon group. At this point, it is preferable that a functional group to be reacted with a source of a hydrocarbon group having a cationic functional group is protected with a protective group such as tert-butoxy or the like.

Next, an amino group of the resultant compound is reacted with the source of the hydrocarbon group having the cationic functional group. It is preferable that an amino group of the source of the hydrocarbon group having the cationic functional group is protected by a tert-butoxy group or the like in advance and the source is activated by succinimide or the like. The reactions are preferably performed in the presence of a catalyst such as tertiary amine or the like.

The above-described reactions can be both performed at room temperature. The reactions may be performed either at elevated pressure, reduced pressure or atmospheric pressure, but is preferably performed at atmospheric pressure because the operation is simple.

After the reactions, the resultant product is deprotected by treatment with an acid such as trifluoroacetic acid or the like, and is purified by a usual method. In this manner, a cationic amino acid type lipid can be obtained. The termination point of the reactions can be confirmed by gas chromatography, high performance liquid chromatography, thin layer chromatography, nuclear magnetic resonance spectrum, infrared absorption spectrum or the like.

The method for producing a cationic amino acid type lipid according to the present invention is not limited to the above-described method. For example, an amino group of a trifunctional core compound may be first reacted with a source of a hydrocarbon group having a cationic functional group, and then the $A^{11}$ or $A^{12}$ part of the resultant compound may be reacted with a source of a chain hydrocarbon group.

Hereinafter, examples of material compounds usable for synthesizing a cationic amino acid type lipid according to the present invention will be shown.

As the source of the chain hydrocarbon group, any compound having a reactive functional group which can be covalently bonded with a trifunctional core compound, for example, an amino group, a hydroxyl group, a carboxylic group or the like is usable with no specific limitation.

As the source of the chain hydrocarbon group having a carboxylic group, a fatty acid is usable. Examples of the fatty acid include acetic acid, propionic acid, butyric acid, valeric acid, isovaleric acid, capronic acid, enanthic acid, caprylic acid, undecanoic acid, lauric acid, tridecanoic acid, myristic acid, pentadecanoic acid, palmitic acid, heptadecanoic acid, stearic acid, nonadecanoic acid, arachic acid, behenic acid, palmitoleic acid, oleic acid, linoleic acid, linolenic acid, arachidonic acid and the like; and branched chain forms thereof. Also included are acid anhydrides and acid chlorides of the above-listed substances.

As the source of the chain hydrocarbon group having an amino group, a straight chain primary amine is usable. Examples of the straight chain primary amine include dodecylamine, tridecylamine, tetradecylamine, pentadecylamine, hexadecylamine, heptadecylamine, octadecylamine, docosylamine, oleylamine and the like; and branched chain forms thereof. An amine such as branched isoprenoid or the like is also usable. As the source of an aliphatic hydrocarbon group having an amino group, a secondary amine is usable. Examples of the secondary amine include N-methyl-dodecylamine, N-methyl-tetradecylamine, N-methyl-hexadecylamine, N-ethyl-dodecylamine, N-ethyl-tetradecylamine, N-ethyl-hexadecylamine, N-propyl-dodecylamine, N-propyl-tetradecylamine, N-propyl-hexadecylamine, dioleylamine and the like; and branched chain forms thereof.

As the source of the chain hydrocarbon group having a hydroxyl group, a straight chain primary saturated alcohol is usable. Examples of the straight chain primary saturated alcohol include lauryl alcohol, cetyl alcohol, stearyl alcohol, behenyl alcohol and the like. Examples of other compounds usable as the chain hydrocarbon group having a hydroxyl group include straight chain primary saturated alcohol such as 1,1-dodecenol, 1-oley alcohol, linolenyl alcohol or the like; branched primary saturated alcohol; branched primary unsaturated alcohol; secondary saturated alcohol; and secondary unsaturated alcohol. Dialkylglycerol obtained by linking such an alcohol to the 1,3-position or 1,2-position of glycerin, and dialkylglycerol formed of a primary saturated alcohol and a primary unsaturated alcohol are also usable.

As the source of the chain hydrocarbon group, a sterol is also usable. Examples of the sterol include cholesterol, cholestanol, sitosterol, ergosterol and the like.

As the source of the hydrocarbon group having a cationic functional group, an amino acid or a derivative thereof is usable. Preferably usable are lysine, arginine, histidine and derivatives thereof. More preferably usable are lysine, arginine and histidine. The "derivative of an amino acid" encompasses compounds obtained as a result of a hydrogen atom contained in the amino acid being substituted with a substituent such as lower alkyl group (methyl, ethyl, propyl, isopropyl, n-butyl, sec-butyl, etc.), aminoalkyl group (aminomethyl, aminoethyl, aminopropyl, aminobutyl, etc.), corresponding oligoaminoalkyl group, hydroxyl group, hydroxyalkyl group (hydroxymethyl, hydroxyethyl, hydroxypropyl, etc.), oligooxyalkyl group (oligooxymethyl group, oligooxyethyl group, oligooxypropyl, etc.) or the like.

B. Molecular Assembly

Next, a molecular assembly according to the present invention will be described. A molecular assembly according to the present invention may be anything which includes a cationic amino acid type lipid described above with no specific limitation. Examples of such a molecular assembly include a polymer assembly, a polymer micelle, an emulsion, a lipid microsphere, a bilayer vesicle (liposome), an assembly having a hexagonal structure, and other tubular assemblies. According to the present invention, a vesicle such as a liposome or the like or an assembly having a tubular structure is preferable from the point of view of encapsulating a useful substance. According to the present invention, the content of the cationic amino acid type lipid is not limited to any specific value, but is preferably 20 to 100 mol %, and more preferably 50 to 100 mol %, based on the total molarity of the lipids included in the molecular assembly.

Other than the cationic amino acid type lipid, the molecular assembly according to the present invention may include any lipid which can form a molecular assembly with a cationic amino acid type lipid according to the present invention and is generally used as a lipid component of a molecular assembly. Examples of such a lipid include phospholipid, fatty acid, sterols, various types of glycolipids and the like.

Examples of the phospholipid include egg yolk lecithin soybean lecithin, hydrogenerated egg yolk lecithin, hydrogenerated soybean lecithin, diacylphosphaditylcholin, diacylphosphaditylethanolamine, sphingomyelin, and the like. Such a lipid may include an unsaturated part such as ene (double bond), in (triple bond), diene, diin, triene or the like, or may include a polymerizable group such as vinyl group, for example, styryl group. The content of the phospholipid is not limited to any specific value, but is preferably 0 to 70 mol %, and more preferably 0 to 50 mol %, based on the total molarity of the lipids included in the molecular assembly.

As the fatty acid contained in an acyl chain of the phospholipid, a saturated or unsaturated fatty acid having a carbon number of 12 to 20 is used. Examples of such a fatty acid include myristic acid, palmitic acid, stearic acid, oleic acid, linoleic acid, linolenic acid, octadeca-2,4-dienoic acid and the like. Instead of a material having a glycerol backbone, a trifunctional amino acid such as glutamic acid or the like, an amphoteric amino acid type lipid having a lysine backbone and the like are also usable. The content of the fatty acid is not limited to any specific value, but is preferably 1 to 70 mol %, and more preferably 5 to 30 mol %, based on the total molarity of the lipids included in the molecular assembly.

To the molecular assembly, a sterol usable as a stabilizer may be added as a membrane component of the lipid vesicle. Examples of such a sterol include all the steroids having a perhydrocyclopentanophenanthrene backbone such as ergosterol, cholesterol and the like. Cholesterol is preferable. There is no specific limitation on the content of the sterol. In consideration of the stability of the vesicular membrane, the content of the sterol is preferably 5 to 50 mol %, and more preferably 15 to 40 mol %, based on the total molarity of the lipids included in the molecular assembly.

There is no specific limitation on the method for producing the molecular assembly, and any generally known method is usable. For example, a liposome may be produced as follows. Powder or thin film of a single type of lipid or a mixture of lipids is hydrated and dispersed, and then subjected to a high pressure extrusion method, an ultrasonic radiation method, a stirring (vortex mixing, homogenizer) method, a freezing and melting method, a microfluidizer method or the like. Alternatively, a single type of lipid or a mixture of lipids is dissolved in an organic solvent, the resultant solution is injected into an aqueous phase, and then the organic solvent such as ethanol, ether or the like is removed at reduced pressure or by dialysis. Still alternatively, a single type of lipid or a mixture of lipids is dispersed in an aqueous phase together with a nonionic surfactant such as sodium cholade, sodium dodecyl sulfate, Triton X, laurylether or the like to form an emulsion, and then the nonionic surfactant is removed by dialysis. Also, a reverse phase vaporization method, an incubation method and the like are usable.

A method for encapsulating a useful substance in such a molecular assembly may be appropriately selected in accordance with the type of the useful substance or the like. In the case where the useful substance is a water-soluble drug, for example, the drug may be dissolved in an aqueous phase at the time of liposome production. Alternatively, after the liposome is produced, the water-soluble drug may be added to an external aqueous phase and introduced to an inner aqueous phase utilizing the transmissive property of the liposome membrane. An unencapsulated water-soluble drug can be separated from the encapsulating vesicle by gel filtration, ultracentrifugation, ultrafiltration or the like. In the case where the useful substance is an oil-soluble drug, for example, the drug may be mixed with a single type of lipid or a mixture of lipids which is in the state of being dissolved in an organic solvent, and the mixture is formed into a liposome by any of above-described methods. In this way, the drug may be introduced to a hydrophobic part of the bilayer. Alternatively, after the liposome is formed, the drug may be dissolved in an organic solvent mixable with water, and the resultant substance may be added to an external aqueous phase to introduce the drug to a hydrophobic part of the bilayer.

The present invention will be more specifically described below in the following examples. However, these examples are not intended to limit the scope of the present invention.

Example 1

Synthesis of the Cationic Amino Acid Type Lipid (A) A benzene solution (100 mL) of p-toluenesulfonic acid hydrate (4.56 g, 24 mmol) was subjected to boiling point reflux at 85° C., and water was removed before the reaction using Dean-Stark apparatus. Glutamic acid (2.96 g, 20 mmol) and hexadecylalcohol (10.7 g, 44 mmol) were added to the reaction solution, and subjected to boiling point reflux for 10 hours while the generated water was removed. As the reaction proceeded, the suspension was gradually dissolved to become transparent.

After the reaction completed, the solvent was removed at reduced pressure. The resultant solution was dissolved in chloroform, and washed with a saturated aqueous solution of sodium carbonate 3 times. The chloroform layer was dewatered with magnesium sulfate. The resultant substance was filtered, and then the solvent was removed at reduced pressure. The residue was recrystallized with methanol at 4° C. to obtain dialkylglutamic acid derivative (1) (yield: 83%) as white powder.

(1)

The analysis results of the dialkylglutamic acid derivative (1) were as follows: Thin layer chromatography (silica gel plate, chloroform/methanol (4/1) (volume/volume): $R_f$: 0.83 (monospot))

Infrared absorption spectrum (cm$^{-1}$): 1737 ($v_{C=O}$, ester)
$^1$H-NMR (CDCl$_3$, 500 MHz, δ ppm): 0.89 (t, 6H, —CH$_3$); 1.25 (s, 52H, —CH$_2$—CH$_2$—); 1.62 (m, 4H, —CO—O—C—CH$_2$); 1.84 (m, 1H, glu α-CH$_2$); 2.08 (m, 1H, glu β-CH$_2$); 2.45 (t, 2H, glu γ-CH$_2$); 3.45 (t, 1H, glu α-CH); 4.06, 4.10 (t, 4H, —CO—O—CH$_2$)

MS (ESI) Calcd: 595.9. Found: 597.3 (MH)$^+$ (B) The dialkylglutamic acid derivative (1) obtained in step (A) (1.0 g, 1.67 mmol) and triethylamine (202 mg, 2.0 mmol)

were dissolved in dichloromethane (30 mL) and stirred at room temperature for 1 hour. Then, lysine (617 mg, 1.4 mmol), histidine (633 mg, 1.4 mmol), or arginine (593 mg, 1.4 mmol), each having an amino acid protected with a t-butoxy group and also each being activated by succinimide, was added thereto and stirred at room temperature for another 6 hours.

After the reaction completed, the solvent was removed at reduced pressure. The resultant solution was dissolved in chloroform, and washed with a saturated aqueous solution of sodium carbonate 3 times. The chloroform layer was dewatered with magnesium sulfate. The resultant substance was filtered, and the solvent was removed at reduced pressure. The residue was recrystallized with methanol at 4° C. and filtered with a glass filter (G6) to respectively obtain a lysine derivative, a histidine derivative or an arginine derivative having a protected amino group.

Fluoroacetic acid (20 μL) was added to each of the resultant derivatives and stirred at 4° C. for 2 hours. After the reaction completed, the solvent was removed at reduced pressure. The resultant solution was dissolved in chloroform, and washed with a saturated aqueous solution of sodium carbonate 4 times. The chloroform layer was dewatered with magnesium sulfate. The resultant substance was filtered, and the solvent was removed at reduced pressure. The residue was recrystallized with methanol at 4° C., filtered and dried to respectively obtain cationic acid amino acid type lipids (2) (80%), (3) (53%) and (4) (43%) as white powder.

The analysis results of the cationic amino acid type lipids (2), (3) and (4) were as follows:

(2): Thin layer chromatography (silica gel plate, chloroform/methanol (4/1) (volume/volume): $R_f$: 0.63 (monospot))

Infrared absorption spectrum (cm$^{-1}$): 1737 ($v_{C=O}$, ester); 1673 ($v_{C=O}$, amide)

$^1$H-NMR (CDCl$_3$, 500 MHz, δ (ppm)): 0.88 (t, 6H, —CH$_3$); 1.25-1.29 (br, 44H, —CH$_2$—); 4.51 (d, 1H, —CO—N—CH—); 7.8, 8.2 (br, 2H, —C—NH$_2$)

(3): Thin layer chromatography (silica gel plate, chloroform/methanol (4/1) (volume/volume): $R_f$: 0.68 (monospot))

Infrared absorption spectrum (cm$^{-1}$): 1737 ($v_{C=O}$, ester); 1673 ($v_{C=O}$, amide)

$^1$H-NMR (CDCl$_3$, 500 MHz, δ (ppm)): 0.88 (t, 6H, —CH$_3$); 1.25-1.29 (br, 44H, —CH$_2$—); 4.51 (d, 1H, —CO—N—CH—); 7.8, 8.2 (br, 2H, —C—NH$_2$)

(4): Thin layer chromatography (silica gel plate, chloroform/methanol (4/1) (volume/volume): $R_f$: 0.62 (monospot))

Infrared absorption spectrum (cm$^{-1}$): 3321 ($v_{N=H}$, ester); 1708 ($v_{C=O}$, amide)

$^1$H-NMR (CDCl$_3$, 500 MHz, δ (ppm)): 0.88 (t, 6H, —CH$_3$); 1.25-1.29 (br, 44H, —CH$_2$—); 4.51 (d, 1H, —CO—N—CH—); 7.8, 8.2 (br, 2H, —C—NH$_2$)

(2)

(3)

(4)

Example 2

(A) Phase Transition Temperature of the Cationic Amino Acid Type Lipid

Each of the obtained cationic amino acid type lipids was dispersed in a simple medium of pure water at 60° C. and used as a measurement sample. 60 μL of a sample solution (lipid concentration: 1 wt %) was encapsulated in a silver pan (sealable type), and the phase transition temperature $T_c$ was measured by a differential scanning calorimeter with the temperature elevation rate of 2° C./min. and the measurement temperature of 20 to 80° C. The measurement results are shown in Table 1.

TABLE 1

Temperature of the gel to liquid-crystalline phase transition

| Compound | $T_c$ [° C.] |
|---|---|
| 1 | 49.4 |
| 2 | 41.2 |
| 3 | 43.7 |
| 4 | 44.8 |

(B) Zeta Potential of the Molecular Assembly Including a Single Type of Cationic Amino Acid Type Lipid The zeta potential of a molecular assembly (1 mg/mL) including a single type of cationic amino acid type lipid (2), (3) or (4) prepared by the extrusion method was measured by a zeta potentiometer (Nano-ZS, Malvern) with 30 mM of a phosphoric buffer solution at pH7.4. The measurement results are shown in Table 2. The zeta potential of each molecular assembly was +37 mV with the cationic amino acid type lipid (2), +45 mV with the cationic amino acid type lipid (3), and lower at +18 mV with the cationic amino acid type lipid (4). From such zeta potentials, it has been clarified that the surface of a molecular assembly formed of a cationic amino acid type lipid is charged positive under physiological conditions.

TABLE 2

Characteristics of cationic vesicles

| Compound | $T_c$ [° C.] | ξ potential [mV] |
|---|---|---|
| 2 | 41.2 | +37 |
| 3 | 43.7 | +45 |
| 4 | 44.8 | +18 |

Example 3

(A) Observation of the Molecular Assembly Including a Single Type of Cationic Amino Acid Type Lipid 10 mg of the cationic amino acid type lipid (2), (3) or (4) was hydrated in 2 mL of pure water and stirred at room temperature for 6 hours. Then, the resultant hydrate was transmitted with pressure through a membrane filter (final pore diameter: 0.22 μm) (extrusion method). Since the 0.22 μm membrane filter had a poor transmittance at room temperature, each lipid dispersion solution was warmed to 60° C. before being transmitted through the filter. After the transmission, the resultant substance was subjected to ultracentrifugation (33,000 rpm, 30 min.) and re-dispersed in pure water to obtain a molecular assembly including a respective cationic amino acid type lipid. The prepared molecular assembly including a respective cationic amino acid type lipid was observed with a transmission electron micrometer (TEM; accelerating voltage: 100 kV).

(B) Molecular Assembly Including the Single Type of Cationic Amino Acid Type Lipid (2)

Figure 1:
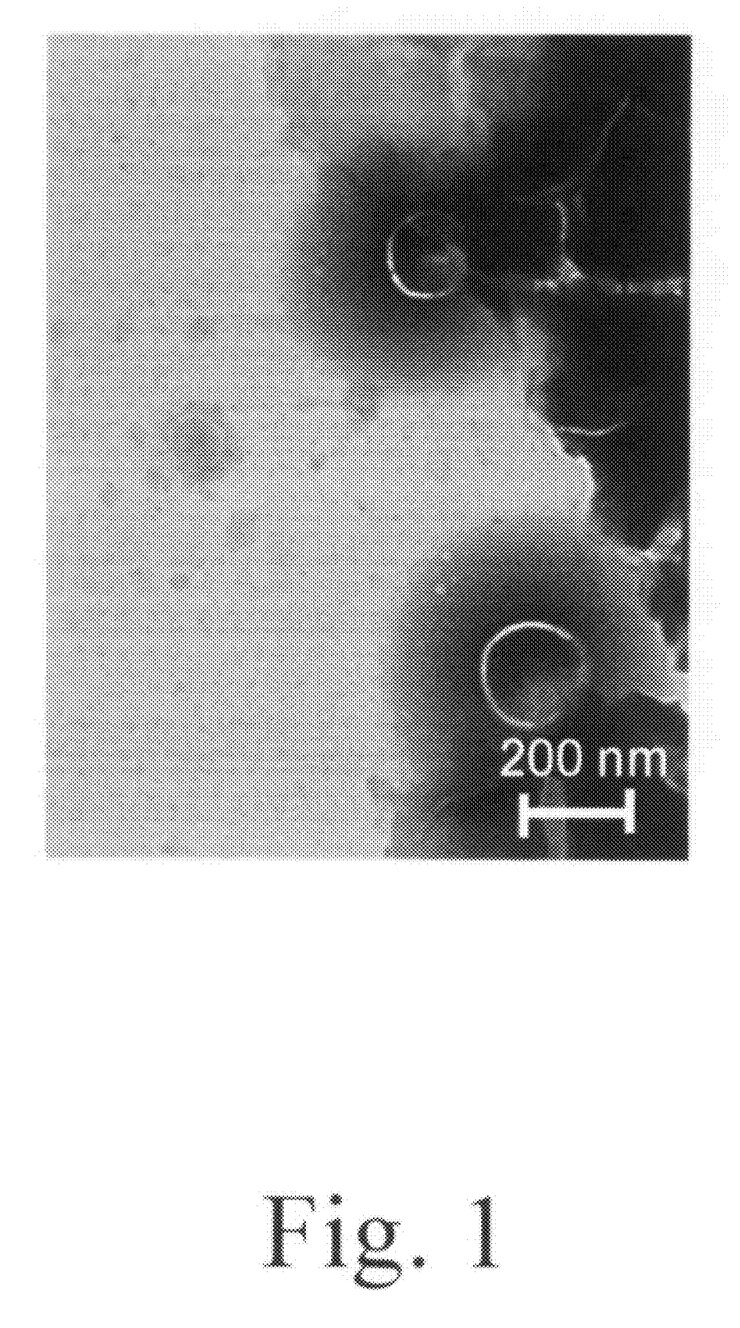
FIG. 1 is a transmission electron micrograph of a molecular assembly obtained by treating a hydrate of a cationic amino acid type lipid (2) with extrusion.

A hydrate dispersion solution of the cationic amino acid type lipid (2) was extruded and observed with an electron microscope. A great number of monolayer vesicles were observed as shown in FIG. 1. The particle size of the vesicles was approximately the same as the particle size thereof measured by a dynamic light scattering method (181±83 nm). Thus, it has been clarified that the cationic amino acid type lipid (2) prepared by the extrusion method forms stable monolayer vesicles.

(C) Molecular Assembly Including the Single Type of Cationic Amino Acid Type Lipid (3)

Figure 2:
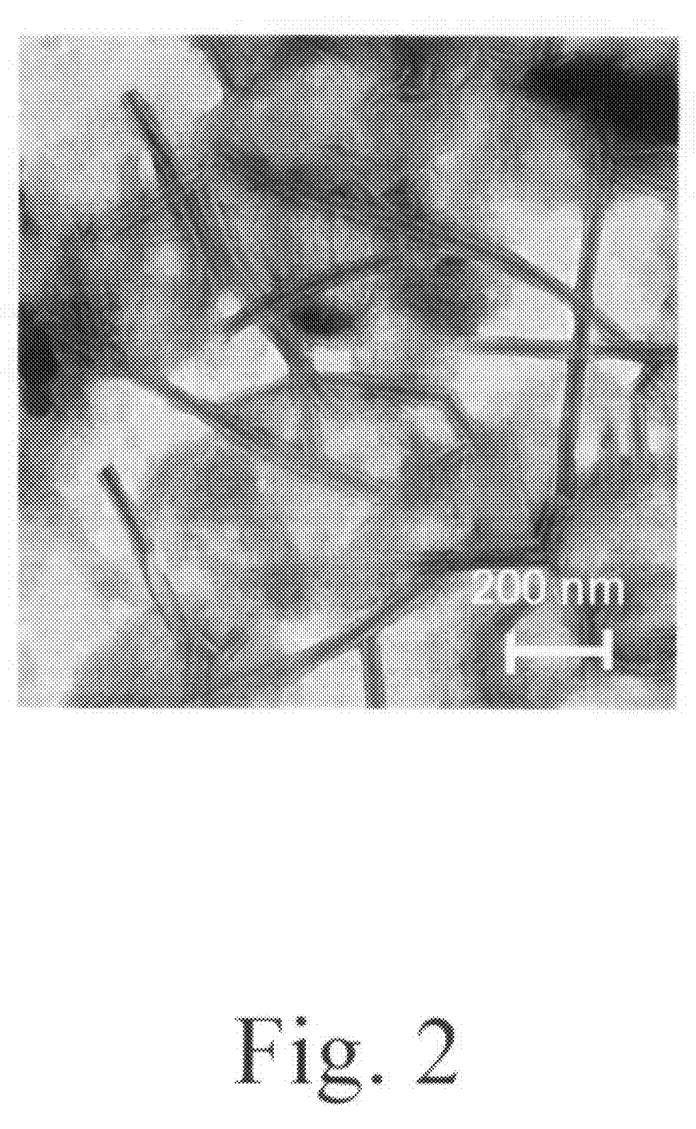
FIG. 2 is a transmission electron micrograph of a molecular assembly obtained by treating a hydrate of a cationic amino acid type lipid (3) with extrusion.

A hydrate dispersion solution of the cationic amino acid type lipid (3) was extruded. While the particle size thereof measured by the dynamic light scattering method was 241±96 nm, a tubular molecular assembly having a diameter of about 20 nm was observed with an electron microscope. As shown in FIG. 2, the branches of the tubular molecular assembly were connected to the stem by hollow parts. The tips of the tube were open. The wall thickness of the tube was about 5 nm, which corresponds to the thickness of the bilayer of the cationic amino acid type lipid (3).

(D) Molecular Assembly Including the Single Type of Cationic Amino Acid Type Lipid (4)

Figure 3:
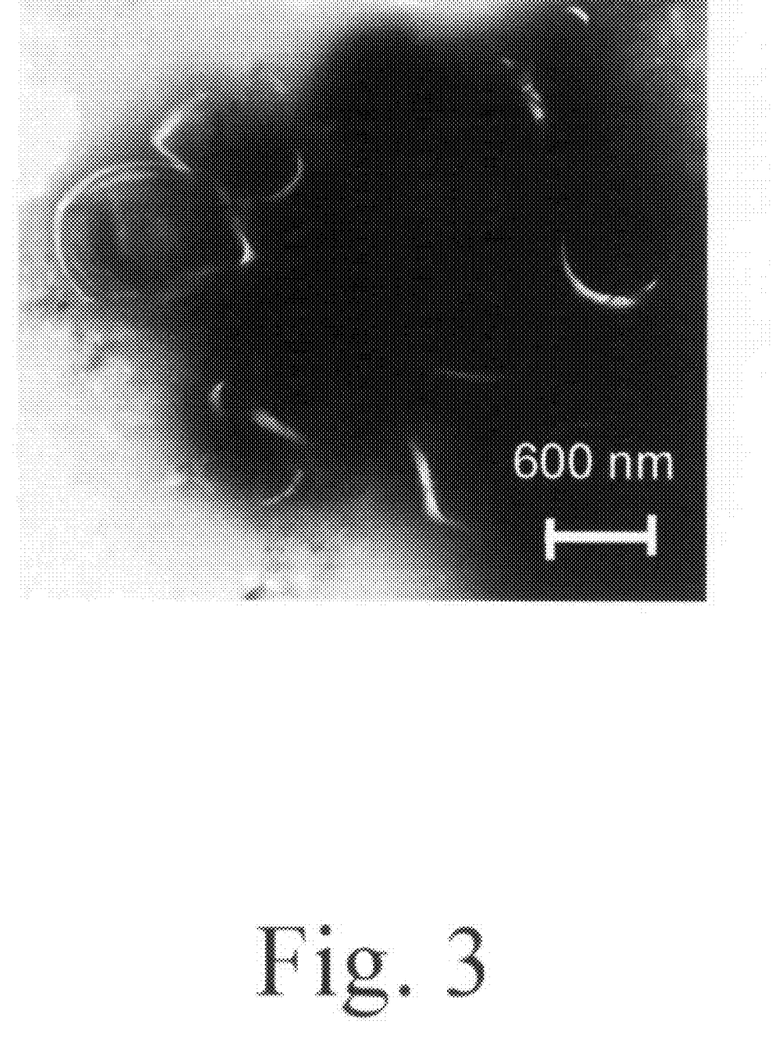
FIG. 3 is a transmission electron micrograph of a molecular assembly obtained by treating a hydrate of a cationic amino acid type lipid (4) with extrusion.

A hydrate dispersion solution of the cationic amino acid type lipid (4) was extruded. With an electron microscope, monolayer vesicle structures having a size of 600 nm to 1 μm were observed (FIG. 3). The particle size thereof measured by the dynamic light scattering method exceeded 1 μm (1647±733 nm). Based on the result that such large monolayer vesicles were observed after the hydrate dispersion solution was transmitted through a filter having a pore diameter of 0.22 μm, it is considered that small monolayer vesicles were immediately aggregated and fused to be grown into large monolayer vesicles.

(E) Analysis of the Cationic Amino Acid Type Lipid (2) and Lys-Asp2C$_{16}$ (5)

According to the present invention, n in general formula (I) is defined as 2 to 4. Especially, glutamic acid in which n is 2 is used, and aspartic acid in which n is 1 is excluded. Meanwhile, as described above, H. S. Kim et al. has reported Lys-Asp2C$_{16}$ (5) in which lysine is linked to dialkylaspartic acid (Hong Sung Kim et al., Gene-Transferring Efficiencies of Novel Diamino Cationic Lipids with Varied Hydrocarbon Chans. *Bioconjugate Chem.* 2004, 15, 1095). The present inventors clarified the difference between the cationic amino acid type lipid (2) and Lys-Asp2C$_{16}$ (5).

Lys-Asp2C$_{16}$ (5) was hydrated at a lipid concentration of 10 mg/mL and transmitted through a membrane filter having a final pore diameter of 0.22 μm by the extrusion method. Then, the phase transition temperature and the particle size of the assembly were measured. The particle size of the molecular assembly of Lys-Asp2C$_{16}$ (5) measured by the dynamic light scattering method was 374±178 nm, and the phase transition temperature thereof was 30° C. It has been found that Lys-Asp2C$_{16}$ (5) has a poorer molecular filled state and is easier to be aggregated than the cationic amino acid type lipid (2).

TABLE 3

Comparison of cationic vesicles

| Compound | Transition temperature [° C.] | Particle size [nm] |
|---|---|---|
| 2 | 41.2 | 188 ± 82 nm |
| 5 | 30.0 | 374 ± 178 nm |

Figure 4:
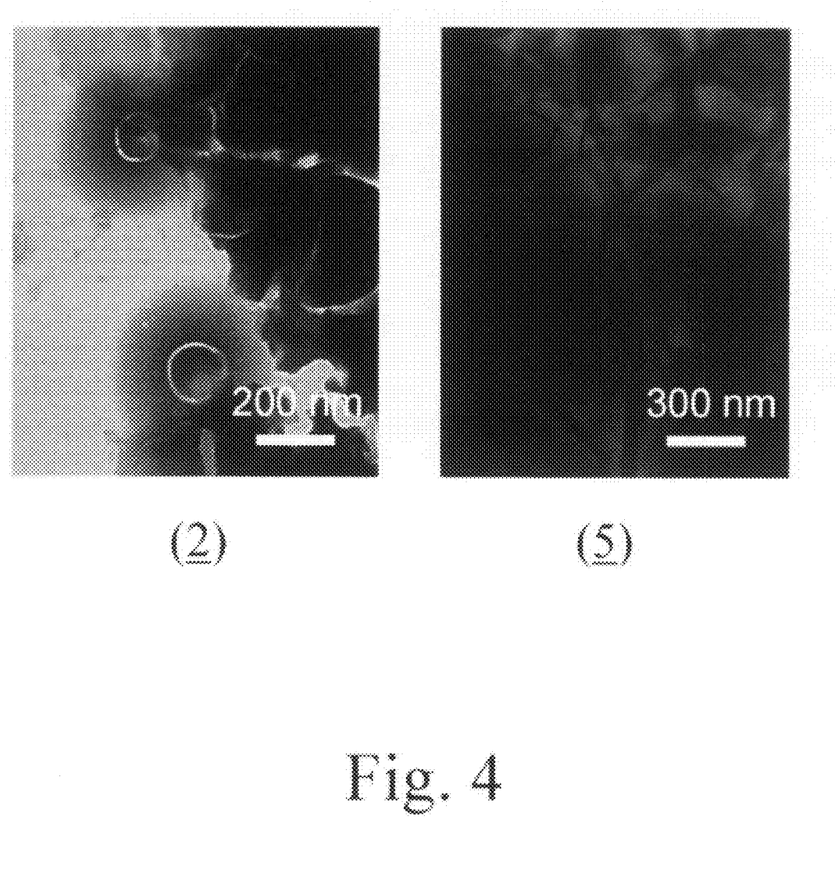
FIG. 4 compares a transmission electron micrograph of the molecular assembly formed of the cationic amino acid type lipid (2) obtained by treating the hydrate with extrusion and a transmission electron micrograph of a molecular assembly formed of Lys-Asp2C$_{16}$ (5).

With a transmission electron microscope (TEM), the cationic amino acid type lipid (2) was observed to have a bilayer vesicle structure, whereas Lys-Asp2C$_{16}$ (5) was observed to be a ribbon-like molecular assembly (FIG. 4). The thickness of the ribbon is considered to be about 5 nm, which is approximately the same as the thickness of the bilayer. The ribbon had a width of about 100 nm and a length of as much as about 1 μm or greater. From these results, it has been clarified that the hydrophobic backbone of glutamic acid and the hydrophobic backbone of aspartic acid are different in the molecular assembly at the time of hydration.

Figure 5:
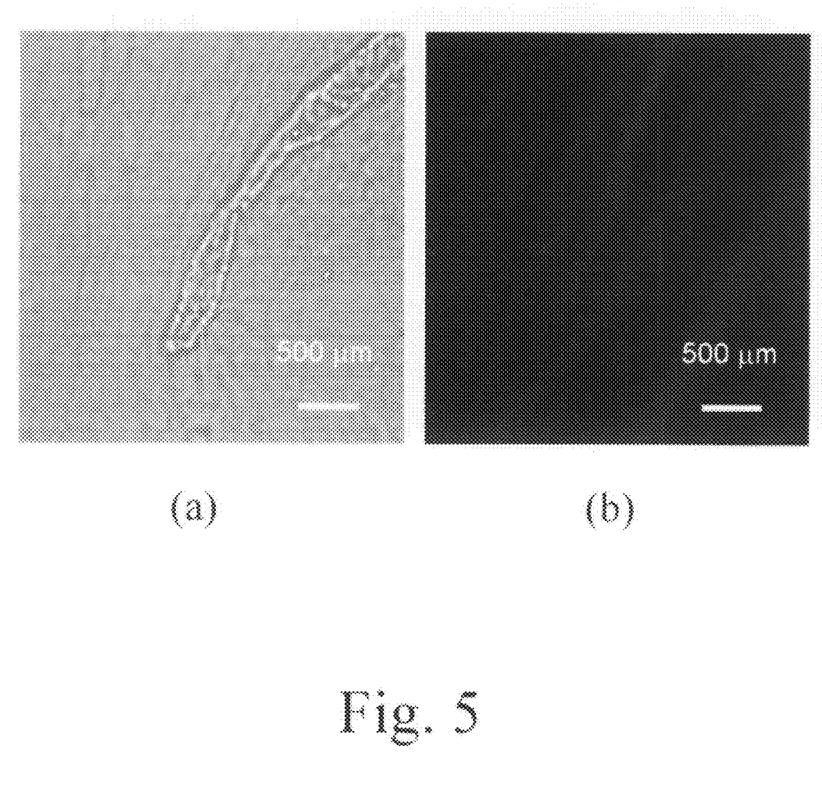
FIG. 5 compares (a) a polarization electron micrograph of the molecular assembly formed of Lys-Asp2C$_{16}$ (5) at 37° C. and (b) a polarization electron micrograph thereof at room temperature.

Since the phase transition temperature of Lys-Asp2C$_{16}$ (5) is 30° C. or the vicinity thereof, the molecular assembly form of Lys-Asp2C$_{16}$ (5) at 37° C. was observed with a polarization microscope. A similar ribbon-like fibrous form was observed, with no significant difference in the form between above and below the phase transition temperature (FIG. 5). Based on the result that polarization was not observed at 37° C., it is considered that the ribbon is in a liquid crystalline state, and is in a gel state at room temperature with polarization being observed.

As a result, it has been clarified that Lys-Asp2C$_{16}$ (5) is unstable in the form and thus is changed into a ribbon-like form having a length of about 1 μm after being transmitted through a membrane filter having a pore diameter of 0.22 μm. It is concerned that when being mixed with another phospholipid, Lys-Asp2C$_{16}$ (5) unstabilizes the structure and the dispersion state of the resultant vesicle.

Example 3

Cytotoxicity Test on the Cationic Amino Acid Type Lipid (2)

Figure 6:
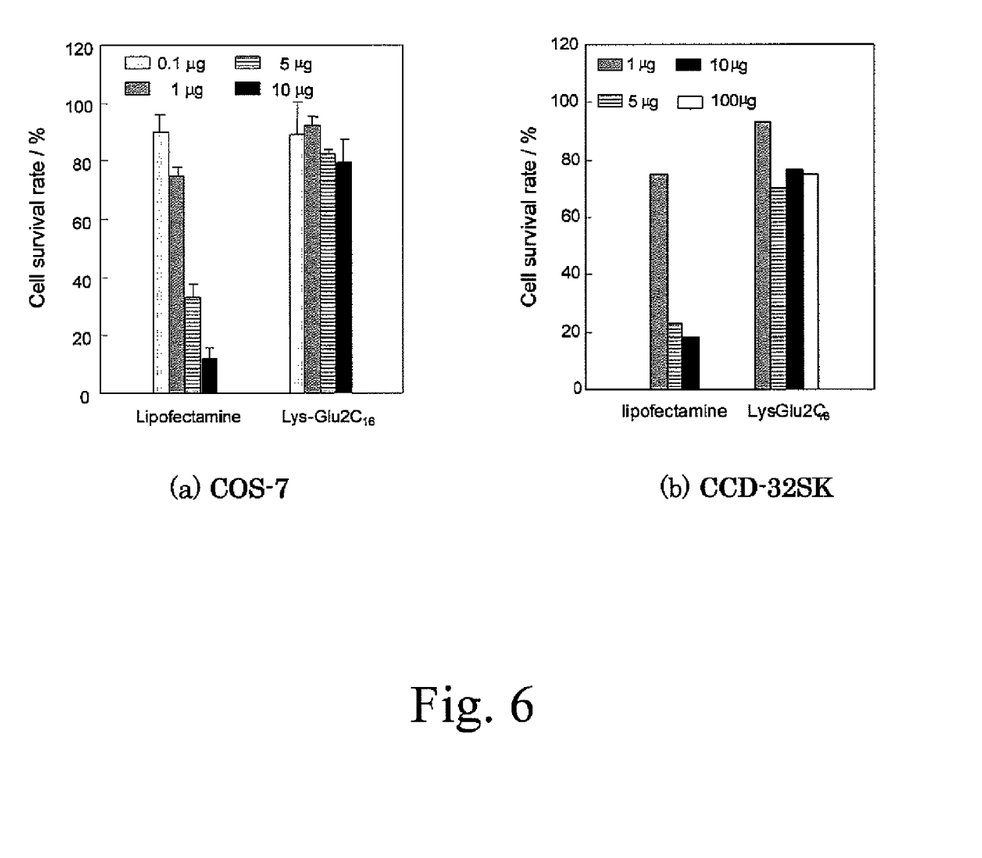
FIG. 6 compares graphs illustrating the cytotoxicity of the cationic amino acid type lipid (2) and lipofectamine based on (a) the cell survival rate of COS-7 and (b) the cell survival rate of CCD-32SK.

The cationic amino acid type lipid (2) was evaluated in terms of cytotoxicity by adding different amounts thereof to cells. Specifically, $1 \times 10^4$ simian kidney-derived cells COS-7 or human fibroblasts CCD-32SK were planted to dishes and cultured for 24 hours in an incubator. To the cultured cells, a cationic liposome diluted with a medium was added so as to be 0.1, 1, 5, and 10 μg/dish. The cells were cultured for another 24 hours. Then, the cells were washed with a medium, and the cell survival rate was calculated by the WST assay. Based on the results, the cytotoxicity was evaluated (n=2). For comparison, the same test was performed using lipofectamine, which is currently in general use as a gene introduction drag. The results are shown in FIG. 6. In the figure, (a) represents the results with COS-7, and (b) represents the results with CCD-32SK. Where 10 μg of lipofectamine was added to COS-7, the cell survival rate 24 hours later was 20%.

With the addition of 10 μg of the molecular assembly including the single type of cationic amino acid type lipid (2) to COS-7, the cell survival rate was not decreased at all. Based on this result it has been clarified that cationic amino acid type lipid (2) is much lower in toxicity than lipofectamine. With CCD-32SK, the cell survival rate was 20% or less when 10 μg of lipofectamine was added, whereas the cell survival rate was about 80% with the cationic amino acid type lipid (2) under the same conditions. Even when 100 μg of the cationic amino acid type lipid (2) was added, the cell survival rate was not decreased. These results indicate that the cationic amino acid type lipid (2) is significantly lower in toxicity than lipofectamine.

INDUSTRIAL APPLICABILITY

A cationic amino acid type lipid according to the present invention is applicable, for example, as a surface improving agent for a liposome, a microsphere, a filler for separation, various types of sensors, a cell culturing substrate or the like, which has a specific recognizability to cells or proteins; and is also applicable to an emulsifier, a stabilizer, a dispersant, a solubilizer, a mixing agent, a penetrating agent, a viscosity adjusting agent or the like of drugs, foods, cosmetics, dyes and the like.

The invention claimed is:

1. A cationic amino acid type lipid represented by formula (I):

(I)

wherein $R^1$ is represented by one of formulas (a), (b) and (c):

$R^2$ and $R^3$ are each independently a $C_{12-30}$ alkyl, alkenyl or alkynyl group, said alkyl, alkenyl or alkynyl group optionally having a substituent selected from the group consisting of alkyl groups, alkenyl groups, alkynyl groups, isoprenoid groups, vinyl groups, carboxyl groups, hydroxyl groups, amino groups and mercapto groups, $A^1$ and $A^2$ are each independently a linkage group selected from the group consisting of —COO—, —OCO—, —CONH— and —NHCO—, and n is an integer of 2 to 4.

2. The cationic amino acid type lipid according to claim 1, wherein $A^1$ and $A^2$ are both —COO—.

3. The cationic amino acid type lipid according to claim 1, wherein $R^2$ and $R^3$ are each independently an alkyl group having a carbon number of 12 to 22.

4. The cationic amino acid type lipid according to claim 1, wherein n is 2.

5. A cationic amino acid type lipid represented by any one of formulas (I)-1, (I)-2 and (I)-3:

(I-1)

(I-2)

(I-3)

6. A molecular assembly including the cationic amino acid type lipid according to claim 1 or 5.

* * * * *